(12) United States Patent
Cuypers et al.

(10) Patent No.: US 7,905,848 B2
(45) Date of Patent: Mar. 15, 2011

(54) HYBRID IMMOBILISATION DEVICE

(75) Inventors: Steven Cuypers, Gravenwezel (BE);
Bogdan Bogdanov, Borgerhout (BE)

(73) Assignee: Orfit Industries, Wijnegem (BE)

( * ) Notice: Subject to any disclaimer, the term of this patent is extended or adjusted under 35 U.S.C. 154(b) by 1152 days.

(21) Appl. No.: 11/097,379

(22) Filed: Apr. 4, 2005

(65) Prior Publication Data
US 2005/0222529 A1 Oct. 6, 2005

(30) Foreign Application Priority Data
Apr. 2, 2004 (EP) ..................................... 04447083

(51) Int. Cl.
*A61F 5/00* (2006.01)
*A61F 13/00* (2006.01)
(52) U.S. Cl. ......... 602/7; 602/5; 602/6; 602/21; 602/61; 128/845; 128/869
(58) Field of Classification Search .................. 602/5–8, 602/27–29, 20–22; 128/845, 846, 849, 857, 128/869, 870
See application file for complete search history.

(56) References Cited

U.S. PATENT DOCUMENTS

| | | | | |
|---|---|---|---|---|
| 4,467,799 A | * | 8/1984 | Steinberg | 128/206.14 |
| 4,821,708 A | * | 4/1989 | Guignard et al. | 602/7 |
| 5,584,800 A | | 12/1996 | Scholz et al. | |
| 5,775,337 A | * | 7/1998 | Hauger et al. | 128/869 |
| 6,210,788 B1 | * | 4/2001 | Cuypers | 428/316.6 |
| 6,595,938 B1 | | 7/2003 | Delmore et al. | |

* cited by examiner

*Primary Examiner* — Kim M Lewis
(74) *Attorney, Agent, or Firm* — Dykema Gossett PLLC

(57) ABSTRACT

A hybrid immobilisation device which is provided to cover at least a part of a patients' body that needs to be supported and/or immobilised, the immobilisation device being at least partly made of a plastic material. The immobilisation device comprises at least one first (1, 11) and at least one second part (2, 12) which are connected to each other in view of forming the immobilisation device, the first part (1) being provided to at least partly cover the body part to be immobilised and being made of a material comprising a first thermoplastic material having a first melting temperature T1, the second part (2) being made of a second material comprising a plastic material having a second melting temperature T2, T2≧T1 to allow for either a separate or simultaneous moulding of the first part (1) and second part (1, 2) after the first and second part have been assembled, the first part (1) being connected to the second part (2) in such a way that the first thermoplastic material and the second plastic material at least partly overlap.

15 Claims, 4 Drawing Sheets

HYBRID IMMOBILISATION DEVICE

BACKGROUND OF THE INVENTION

1. Field of the Invention

The present invention relates to an immobilization device which is provided to cover at least a part of a patient's body that needs to be immobilized and/or supported, the immobilization device being at least partly made of a plastic material.

2. The Prior Art

Immobilization and adaptation devices are frequently used in orthopedic applications, in the immobilization of inflamed or injured joints in case of trauma or diseases, for the support and immobilization of ligaments and muscular structures and in physical rehabilitation applications, and in podiatry, for example, as insole (foot-bed) applications.

Immobilization devices also know a wide use in radiation therapy and diagnostic imaging. Especially in diagnostic imaging and radiation therapy, proper immobilization and reproducible positioning of the part of the patient's body to be treated with respect to the radiation source is of vital importance. In radiation therapy it is a prerequisite to ensure that the radiation is delivered exactly at the target position where it is needed, while minimizing the risk to exposure of surrounding healthy tissue. Reproducible positioning is of utmost relevance in fractionated treatment, where a radiation dose is divided into a multiplicity of sub doses which are delivered to the patient at different directions and on different points in time, to allow for a maximum recovery of healthy tissue and to minimize complicat ions from overexposure to radiation. To simultaneously achieve reproducible positioning and limit the possibility of displacing the body part in the course of the treatment, the position of the body part is fixed using a immobilization device which is moulded to correspond as accurate as possible to the shape of the body part.

In the art a wide variety of plastic materials has been used in the casting of orthopaedic structures, rehabilitation technique aids, radiation therapy fixation and imaging fixation. However, only a few of these known materials are suitable for direct moulding to the patients' body because of their low melting temperature and good mouldability and elasticity in the molten state. The majority of the engineering plastics have a melting temperature which is above 100° C. These materials may be suitable for use in immobilisation structures as well, provided they are moulded to a positive mould corresponding to the part of the patients' body that needs immobilisation. The use of such materials however involves the additional step of making the positive mould.

A plurality of existing techniques is disclosed in U.S. Pat. No. 5,584,800. A first disclosed technique in which a knit fibre glass fabric is impregnated with a polyurethane resin, presents the disadvantages that fibre glass insufficiently adapts to the fine structure of the body and besides this often obstructs x-rays, thus interfering with the x-ray image. Polyester fabrics used in stead of glass fibre fabric show an inferior strength-to-weight ratio. According to the noted patent, other known fixation devices are made of a thermoplastic material, which is heated to a temperature above its softening point and than moulded over the body part to be immobilized, to provide the best fit to this body part. The use of thermoplastic material ensures that optimal adaptation of the fixation device to the body part involved may be achieved.

The inventor has however observed that with an immobilisation device made of one single thermoplastic material, the stability of the device is still insufficient and provides insufficient guarantee that the displaceability of the body part is restrained to less than 0.5 to one or a few mm. This has the consequence that adjusting the patient positioning is insufficiently accurate as well as the reproducibility of the patient positioning.

Still other known immobilisation devices are made of plastic material with higher melting temperatures, e.g. polyethylene (PE), polypropylene (PP), polyvinylchloride (PVC) which is moulded into a standard shape, and made available in a single size or a few sizes. To allow some adaptation to the body part and to provide for an improved fit, the device comprises for example Velcro® strips, with which parts of the device may be pulled towards each other and releasably fixed in that position. These immobilisation devices however present insufficient fit and insufficient comfort. The insufficient fit entails the risk that the immobilisation provided is insufficiently adequate and accurate.

There is thus a need to an immobilisation device the shape of which shows an improved adaptability to the body part that needs immobilisation and to the position in which the body part is to be immobilised.

It is therefore the aim of the present invention to provide an immobilisation device which is suitable for use in a wide variety of applications, for example orthopaedics, physical rehabilitation, diagnostic imaging and radiation therapy and podiatry. It is further the aim of the present invention to provide an immobilisation device which shows an improved adaptability to the body part that needs immobilisation and to the position in which the body part is to be immobilised.

SUMMARY OF THE INVENTION

The immobilisation device of this invention is characterised in that it comprises at least one first and at least one second part which are connected to each other in view of forming the immobilisation device, the first part being provided to at least partly cover the body part to be immobilised and being made of a material comprising a first thermoplastic material having a first melting temperature T1, the second part being made of a second material comprising a plastic material having a second melting temperature T2, T2≧T1, to allow for either a separate or simultaneous moulding of the first part after the first and second part have been assembled, the first part being connected to the second part in such a way that the first thermoplastic material and the second plastic material at least most partly overlap.

By combining at least two materials in an immobilisation device as is done in the present invention, the entire immobilisation device or only first part may be shaped by (1) heating either the entire device or only the first part to the temperature needed to melt or soften either the first and second part or only the first part so that it becomes mouldable, (2) moulding either the first and second part or the first part alone on the patient's body and (3) allowing either the entire immobilisation device or the first part alone to cool in the moulded shape.

By dividing the immobilisation device in at least two parts which at least partly overlap, the properties of each part may be individually optimised, while there is a minimum risk to adversely affecting the functioning and properties of the other part. The first part usually has the function of covering and restraining the body part to be immobilised or supported in a specific position. By having this first part made of a first thermoplastic material, optimum adaptability to the shape and/or position of the body part to be immobilised at low temperature and adequate moldability in the molten state can be ensured, so that the first part can be shaped to match the shape of the patients' body as close as possible.

By combining two materials the first and second part may each be dimensioned and designed in such a way that the majority of the fixation force provided by the device is exerted to the solid parts of the body. In a practical example this means that the first part would be designed to cover and exert a fixation force to the bone structure, and that the second part is provided to fix the position of the first part. Thereby the first part can be designed such that weak tissue is covered and subjected to fixation forces to only a minimum extent, in view of improving comfort to the patient.

In the preferred embodiment where the second material has a different density than the first material, in particular a lower density, the second part will usually be provided to cover at least part of the body part covered by the first part of the immobilisation device. This embodiment serves the purpose of improving the rigidity of and stabilisation provided by the immobilisation device. In this preferred embodiment it may be particularly preferred that the first and second material have a melting temperature which is virtually the same, to allow for a simultaneous moulding. However a small difference in the melting temperature will not be detrimental to the invention.

The immobilization devices known from the art are designed to not only cover and exert a fixation force to the body part that is to be immobilized. The immobilization devices known from the art are designed to a larger part of the patient's body, hard bone structure as well as weak tissue. This is uncomfortable to the patient, the more since the fit of prior art devices is determined by the shrinking shown by the thermoplastic material during cooling after it has been moulded to the body part.

In the preferred embodiment where the second part of the device has the function of fixing the position of the first part with respect to the patient's body and/or a support or diagnostic or therapeutic device, this function may be optimized by having the second part made of a plastic material having a second melting point T2 which is higher than the first melting point T1 of the first thermoplastic material, as this allows minimizing the risk to deforming the second part while melting and moulding the first part. In particular, when T2>T1 there is a minimum risk that the function of the second part, such as stiffness and rigidity get altered. This is important as these properties contribute to the stability of the device and to limiting the displacement of the body part that needs immobilization or support within the device. In particular, it is important that the second plastic material melts, softens or stretches to a minimum extent at the melting temperature of the first thermoplastic material to minimize the risk to changing the properties of the second material.

The device of the present invention presents the advantage that it may be re-moulded after it had been shaped a first time to fix the position of the body part in a first position. The re-moulding is achieved by re-heating the device to the melting temperature of the first thermoplastic material, followed by moulding the first part to the patient's body. This may for example be relevant in case of rehabilitation where in a first period limbs should be immobilised in a first position, followed by a second period of time where limbs immobilisation in a second position, different from the first position, should be done. Also, the immobilisation device of this invention presents the advantage that it is re-sizeable and allows patient adaptation. This may be of importance in case the size of the body part that needs immobilisation changes in the course of the treatment period. This is also important in case the immobilisation device is available in a single or a few sizes only. Furthermore, as the thermoplastic material is re-mouldable, the immobilisation device can be personalised and nevertheless be available at an economically feasible cost.

In the immobilisation device of this invention, the first and second part are connected to each other. The connection may be effected through any suitable connecting technique known to the person skilled in the art, for example by means of welding, gluing, melting together and stitching or a combination of two or more of these techniques. However, any other technique ought suitable by the person skilled in the art may also be used. Thereby, the first and second part may overlap.

An additional preferred embodiment of the immobilisation device of this invention is characterised in that at least part of one or more of the first and second part is associated with a further material. The further material will be selected by the person skilled in the art taking account of the envisaged properties of the immobilisation device. For example if it is envisaged to improve protection of certain body parts from irradiation, corresponding parts of the immobilisation device may comprise a material which has a low radiation transparency. In another preferred embodiment, a dosimeter is connected at one or more specific positions of the second material to measure the radiation to which the patient is exposed, or foam material is connected to the first or second part to improve the patient comfort or to decrease the side effects of the irradiation treatment.

DETAILED DESCRIPTION OF THE PREFERRED EMBODIMENT

Figure 1A:
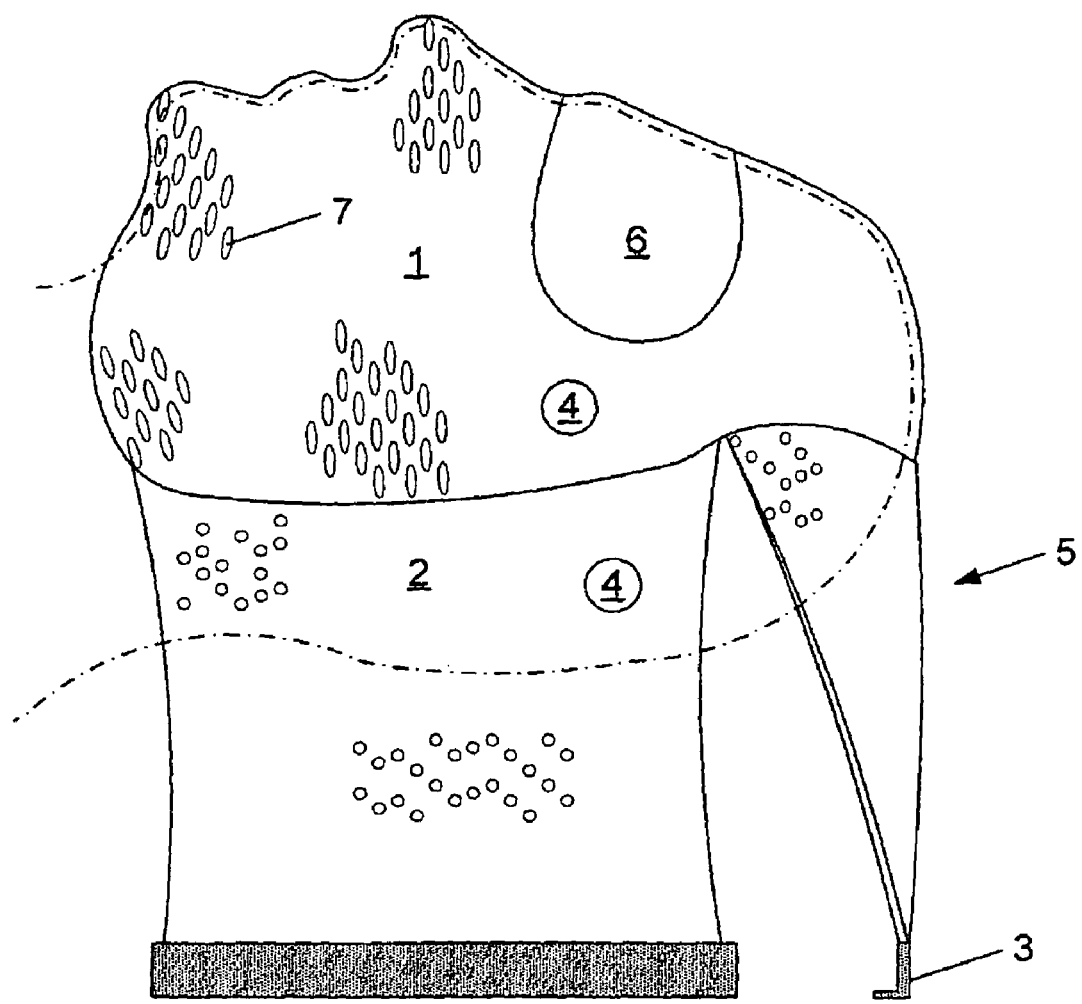
FIG. 1a shows a view to a preferred embodiment of a head fixation mask.

In the following description an immobilisation mask for immobilising the head of a patient in radiation therapy and/or diagnostic imaging is described, as well as an orthosis for immobilising the position of a thumb or a finger with respect to the hand. However, it will be understood by the person skilled in the art, that the device of this invention is also suitable for fixing the position of any other body part, for example a leg, a part of a leg or any other body part.

The immobilization device shown in FIG. 1 is a head fixation mask 5 for immobilizing a patient's head. The immobilization device 1 comprises a first part 1 provided to cover the face of the patient. The first part 1 is delimited by an edge 9. The first part 1 is connected to three second parts 2, 2a, 2b and 2c, at specific positions on the edge. Part 2a and 2b are positioned along opposite longitudinal sides 20 of the first part 1 of the mask 5. Part 2c is positioned along the top edge 21 of first part 1 of the mask, and significantly contributes to the fixation of the position of the head. According to the present invention the material of the first part 1 and the second part 2 may overlap to a certain extent. This may for example be done in view of facilitating the connection, or to imply specific mechanical properties to the overlapped zones of the first part 1. If so desired, the immobilization device may comprise a plurality of first parts 1, or the first part 1 may be made of a plurality of sub-parts made of the same or different materials. The first parts 1 may be intercom-nected and/or connected to the second parts 2. If so desired, depending on the circumstances in which the mask 5 is to be used, the number of second parts 2 may be increased or decreased. If so desired the second part 2 may in turn be made of a plurality of sub-parts that are connected together to form the second part. The sub-parts 2 may be made of the same or a different material.

Figure 3:
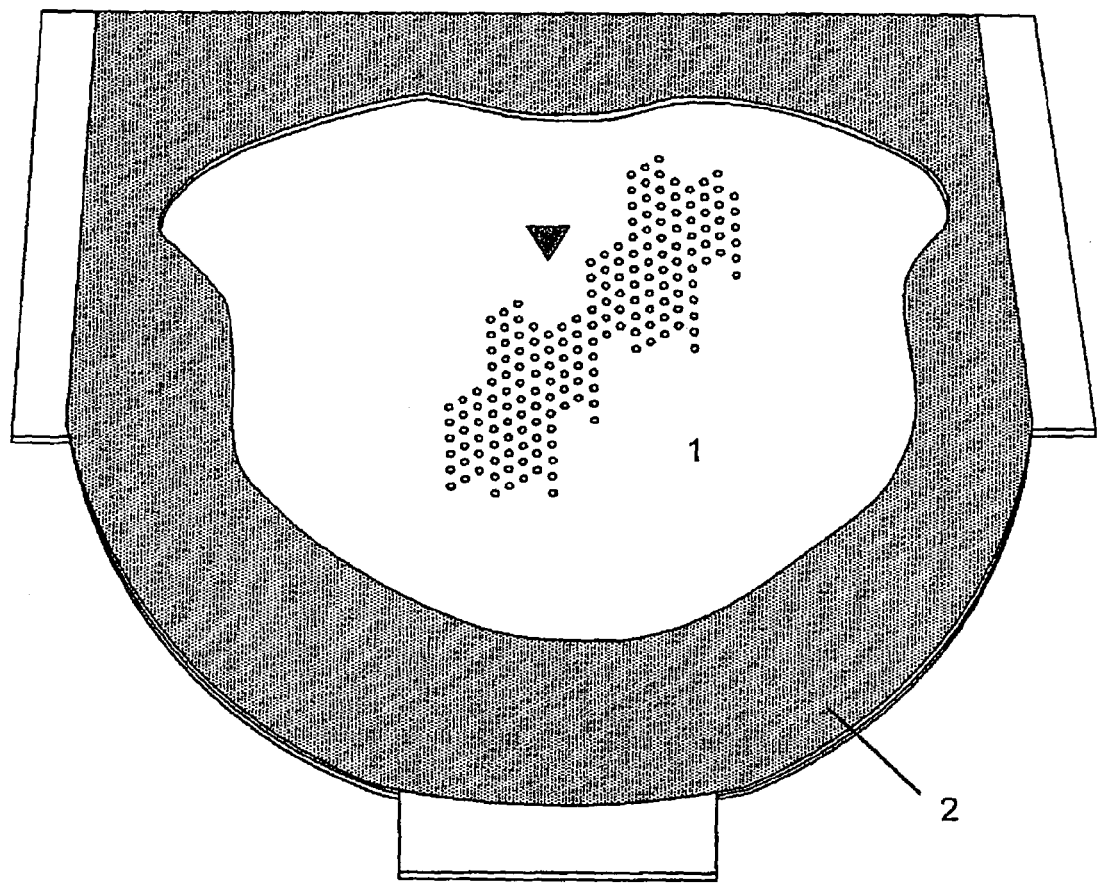
FIG. 3 shows an alternative embodiment of this invention where the first and second part partly overlap.

FIG. 3 shows an alternative embodiment of the immobilisation device of this invention made as a multi-layer device. In this device the first part 1 takes the form of a first layer made of a first material, which is connected to and partly covered by a second layer 2 of a second material forming the second part.

In radiation therapy or diagnostic imaging it is important to sufficiently stabilise and reproduce the fixation of a treated body part to minimise exposure of surrounding healthy tissue. An improved control in this respect may be achieved if the second material is designed in a way to increase the rigidity and stability of the fixation device. As can be seen from FIG. 3, in such a case the second material 2 will usually have a lower density than the first material and will function as a reinforcement layer to the first material and it does not effect substantially the radiation transmission of the fixation device. To achieve this the second part 2 may partly or entirely be made of a foamed material. The foamed material of the second part 2 may take the shape of a single layer. However, the immobilisation device may comprise further layers of the same or different foamed materials to improve comfort to the patient, improve the rigidity and stability of the device once moulded and to control radiation transmission through the material. In case the first and second layer are made of the same material, both materials may be connected by melting them and contacting them in the molten state. The immobilisation device can then be made by moulding the multi-layer material to the body part to be immobilised. In case the immobilisation device is not intended for use with radiation, comfort to the patient may be improved by making the second part of one or more layers of foamed material.

The first 1, 11 and second 2, 12 part may be connected to each other by any suitable technique known to the person skilled in the art for connecting plastic materials. Suitable techniques include welding, gluing, melting together, stitching or a combination of two or more of these techniques. The person skilled in the art will be capable of selecting the most suitable connecting technique, depending on the envisaged application and the nature of the material of which the first 1, 11 and second 2, 12 part are made. Depending on the nature of the immobilisation device, the number of second parts may be varied.

When analysing the problems occurring with existing immobilisation devices, the inventor has found that the part of the immobilisation device covering the body and the parts of the immobilisation device connecting the body covering parts to a support surface or to each other should meet different requirements. Often, opposing requirements which cannot be combined in one single material, are to be met by different parts of the immobilisation device. For example when moulding a mask, the part of the mask covering the face should be mouldable and stretch somewhat to allow it matching the contours of the face as good as possible, if accurate fixation is envisaged. The parts of the mask connecting this part to the support surface on the other hand, should be as rigid as possible and stretch as few as possible. By making the immobilisation device of at least two parts, each part being made of a different material, this problem can be overcome.

The first part 1 is made of a material comprising a first thermoplastic material which is mouldable at a temperature that can be supported by the body. Thereto, mostly use will be made of a thermoplastic material having a melting point of below 100° C., preferably between 60-70° C. As the first thermoplastic material, any thermoplastic material or blend of two or more thermoplastic materials ought suitable by the man skilled in the art may be used. The first thermoplastic material is preferably selected from the group of polyurethane; polyisoprene; polyester for example polycaprolactone; a blend of one of these materials with another polymer for example a blend of a polyester, for example polycaprolactone with different polymers; copolymers or blends or combinations of two or more of these materials. The use of these materials is preferred as they have relatively low softening temperatures, the material thus being suitable for direct moulding to the patient's body. Polycaprolactone shows a good compatibility with a wide variety of materials. Besides the above mentioned materials some or the polyolefins having side chains of cyclic hydrocarbons, show the combination of a sufficiently low melting or softening temperature and sufficient rigidity. The person skilled in the art will be capable of selecting the most appropriate thermoplastic material having a melting point below 100° C. from the available materials.

In this invention, the first part 1, 11 may be entirely made of a single thermoplastic material. It is noted that the first thermoplastic material may be used in the form of a single or a plurality of sheets of the same or different thermoplastic materials, which are connected to each other. It is noted that the first part 1 may for example also be made of a fabric impregnated with one or more of the above described thermoplastic materials. The person skilled in the art will be capable of selecting for the first part 1, 11 a thermoplastic material which is sufficiently stretchable in the molten state so as to ensure optimum fit to the shape of the body part to be covered and immobilised by it shows a limited elasticity and sufficient stiffness and rigidity in the solid, non molten state.

To improve comfort to the patient, the first thermoplastic material may take the shape of a web or a net and will usually comprise a plurality of holes 7 to allow evaporation of moisture from the skin when using the mask. The thickness of the first thermoplastic material will mostly vary between 0.5-5 mm, preferably between 1-4 mm depending on the envisaged rigidity and stiffness, and on the porosity or number and size of the perforations 7 present as these have been found to lower the rigidity and strength of the material. The person skilled in the art will be capable of selecting among the known materials, the material showing sufficient comfort, combined with minimum elasticity after moulding. When the immobilization device is made as a bi-layer or multi-layer device, in which the layer of the first material is combined with a layer of a foamed or expanded second material as the second part, which partially covers the surface of the first material, the thickness of the second material will usually vary from 0.5-5 mm, for example from 1-2 mm.

The above-described materials show an easy forming to a smooth surface showing small scale irregularities (e.g. the nose, ears, eyes, mouth etc), good conformity to the body, low risk to the formation of wrinkles or other defects imparted by the manual moulding and minimum flow when not supported by a supporting material. Furthermore, these materials appear to show some mouldability and elasticity in the molten state, as a consequence of which shaping is facilitated even with a body part showing large degree of irregularity, and an improved fit to the body part to be covered.

A preferred embodiment of the device of this invention is characterised in that the second part 2, 12 is made of a material comprising at least one plastic material, and having a melting point $T2 \geqq$ the melting point of the first material $T1$. If it is the intention to provide for a separate moulding of the first and the at least one second part, it is preferred that T2>T1. The person skilled in the art will be capable of selecting from the existing plastics, those materials that do virtually not soften or melt at the melting temperature of the first thermoplastic material. The second plastic material will usually be selected from the group of thermosetting or thermoplastic materials or a combination or a blend of two or more of such materials, having a melting temperature above the melting temperature of the first thermoplastic material.

Suitable materials for use in the second part 2, 12 are selected from the group comprising polyolefines, for example polyethylene, polypropylene, or ethylene-propylene copolymers; polyvinylchloride; polystyrene; polyamide; polyester for example polyethylenethereftalate, polyethyelvinylacetate; polyurethane or polyesterurethane; polycarbonate, or polyacrylate or copolymers or blends of two or more of these materials. These materials may also be used in a porous, foamed or expanded form. In case the patient or his skin needs to be at least partly observable from the outside, the second material is characterised in that the second part is made of a transparent plastic material, for example a transparent material of the above mentioned materials. Unfortunately up to now, no transparent commercial plastic materials have been found which are available at a reasonable price, have a low melting point below 100° C., and good mouldable properties at this temperature, and combined with sufficient mechanical properties such as good rigidity. The rigidity contributes to the fixation and support of the body part by the immobilisation device.

The second part 2, 12 will similar to the first part 1, 11, usually be made of a single sheet or a plurality of superimposed sheets of the same or different materials which are connected to each other. The use of superimposed sheets for example may assist in locally adapting rigidity or stiffness or any other property of the immobilisation device. The second part 2, 12 may also be made of pieces of two or more different materials that are connected to each other along the sides. It is however also possible to make the second mask part of a fabric impregnated with one or more of the afore described plastic materials. The person skilled in the art will be capable of selecting from the existing plastic materials those materials that are capable of meeting the requirements and envisaged properties of the intended application. For example, the person skilled in the art will be capable of selecting the materials having the appropriate density, thickness and perforation.

As the second material usually a plastic material will be chosen having good rigidity and sufficient stiffness at the temperature at which the device is used, to improve the stability of the mask alone or in combination with the first material. The wording stability of the mask refers to the ability of the immobilisation device of limiting the displacement of the body part within the immobilisation device within a range that is as small as possible, for example <0.5 or 1 mm, though still sufficiently comfortable to the patient. The wording stability also refers to the accuracy, and reproducibility of the positioning of the immobilisation device in fractionated treatment, which is extremely important in diagnostic imaging and radiation therapy. To achieve these properties, the person skilled in the art will be able of selecting from the above mentioned second plastic materials, the material Depending on the envisaged strength of the immobilisation device 5, the second part 2 may also comprise or be made of a fibre reinforced thermoplastic or thermosetting material. Suitable fibre reinforcing materials include glass fibre, carbon fibre, natural fibres for example cotton or wood fibre, synthetic fibres for example polyester, polyamide, aramide fibre or any other suitable fibrous reinforcing material known to the person skilled in the art. The fibrous reinforcing material may be used in different forms, for example loose fibres, fibre yarns, tows or strands, as a knitted, woven or non-wove fabric or any other suitable form known to the person skilled in the art. The use of a composite material will for example be relevant in case the immobilisation or supporting device is intended for immobilising a foot or a leg, where a high strength is required, and weight bearing properties combined with good shock resistance.

The immobilization device shown in FIG. 1 is moulded to a patient's face by heating the immobilization device to a temperature above or in the vicinity of the softening or melting temperature of the first thermoplastic material, where the thermoplastic material becomes sufficiently flexible and mouldable to be shaped over the patient's head. At that temperature, the rigidity of the second material will remain virtually unaffected. The immobilization device 5 is applied to the patient's head, the first part 1 is shaped to follow the contours of the patient's face as good as possible. The connecting means 3 are connected to a support surface, supporting the patient. The mask is allowed to cool, in the course of which the thermoplastic material will shrink, so that a tight fitting of the thermoplastic material to the face is achieved.

The device may be heated in any suitable way known to the person skilled in the art, for example in an oven, or in hot water. To optimise fixation, the material used for the second part 2 and/or the connecting means 3 has a sufficiently high rigidity. This may for example be achieved by increasing the thickness of the material or by connecting to the immobilisation device, means for adjusting the force pulling the immobilisation device to the support surface or pulling several parts of the immobilisation device to each other.

To imply specific properties to the mask 5, the first part 1 may be associated with one or more further materials 4, 6. For example, the first part 1 may locally comprise an amount of material 4 which is not transparent to radiation, so as to limit exposure of the corresponding body part. The further material 4 may be applied on top of the thermoplastic material of which the first part is made or may be incorporated or countersunk therein. In another example, one or more dosimeters 6 may be applied to the mask 5 when it is desired to measure the radiation to which the face has been exposed. The further material may for example also be a water absorbing material or foam material, applied to the side of the mask 5 which contacts the patients' body. However any other further material 6 ought suitable by the person skilled in the art may be used.

In the embodiment of FIG. 1, the second part 2 is made of a transparent polymer. This is done to facilitate positioning of the mask 5. The use of such transparent material allows visualising marks applied to the skin of the patient, which for example assist in improving the positioning of the patient. Such transparent materials may however also be used in other applications.

Figure 1B:
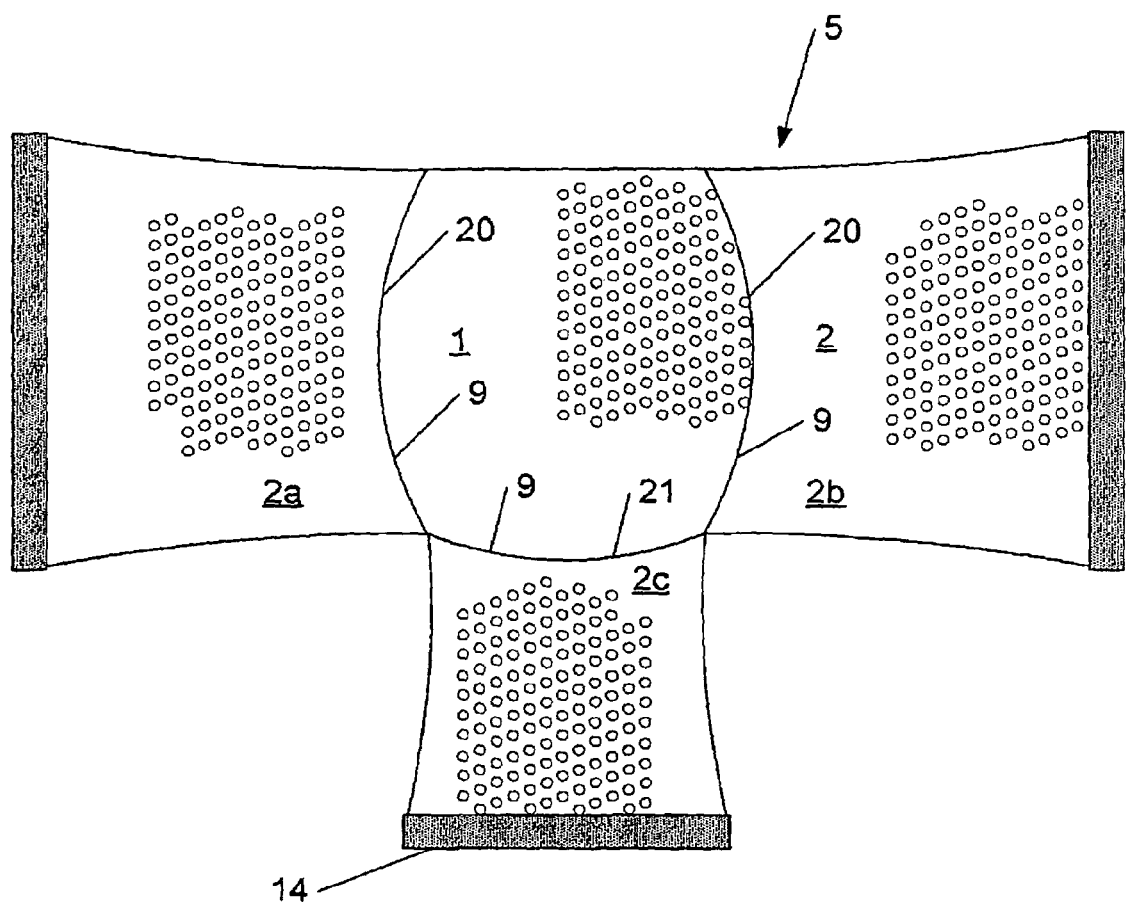
FIG. 1b is a top view to the fixation mask of FIG. 1a, in the flat pre-moulded position.

The second part 2 of the mask 5 shown in FIGS. 1a and 1b comprises connecting means 3 for connecting the mask to the support surface for the patient's head. As connecting means 3 any means thought suitable by the person skilled in the art may be used. The connecting means may be made of any material ought suitable by the person skilled in the art. However, preferably they are made of plastic material, but can also be made of textile, wood or any other suitable material. The second 2 mask part may be connected to the connecting means by any technique ought suitable to the person skilled in the art. Suitable techniques include welding, gluing, melting together, stitching or a combination of two or more of these techniques.

Figure 2:
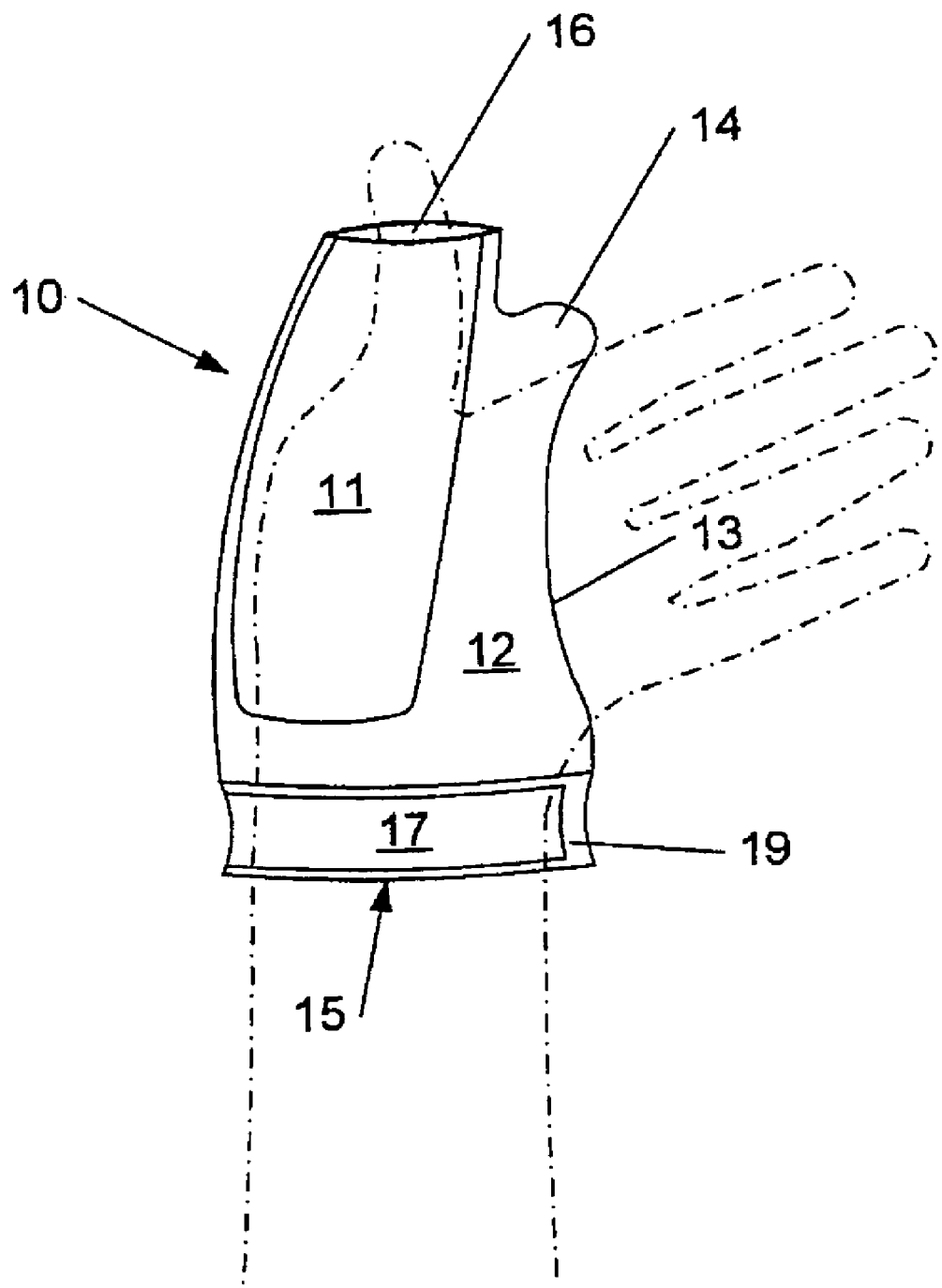
FIG. 2 shows a view to an orthosis for immobilising a finger in a pre-determined position.

The orthosis 10 shown in FIG. 2 is suitable for fixing one or more fingers or the thumb in a specific position with respect to the hand. However, the orthosis 10 may take the shape of any other body part that needs immobilisation or support, for example a leg or a part of a leg, a foot or part thereof, an arm or part thereof. In the particular embodiment shown, the orthosis 10 comprises a body 14. The body 14 comprises a longitudinally extending first hole 13, a second hole 15 at the bottom, a slit 16 to allow opening of the orthosis and inserting the wrist, and a wrist part 19. The orthosis 10 further comprises connecting means 17 to allow tight fitting of the orthosis around the wrist. In the example shown, Velcro™ was used. However any other suitable connecting means may be used. The thumb usually extends through the body part 14 and top hole 16.

Likewise to the immobilisation device of FIGS. 1a and 1b, the orthosis 10 shows a first part 11 and a second part 12. The first part 11 is made of a material comprising a thermoplastic material, which is mouldable at a temperature that can be supported by the body as disclosed above. The second part 12 is pre-shaped and is made of a regular plastic material which is not mouldable at body temperature and has a higher melting point than the thermoplastic material of which the first part 11 is made, as disclosed above.

The first part 11 is moulded to take the shape and size of the thumb or other body part by heating the orthosis 10 to a temperature which corresponds to a temperature at which the first thermoplastic material is mouldable. Usually thereto, the orthosis 10 will be heated to a temperature which corresponds to the melting point of the thermoplastic material of the first part 11, and below the melting temperature of the plastic material of the second part 12. After the heating has been terminated, the hand is inserted into the orthosis 10, by inserting the thumb through the side 13 into the hole 16, the connection between thumb and hand extending from the first hole 13. The orthosis 10 is fit tightly around the wrist and thumb by fastening the connecting means 19. Upon cooling, the thermoplastic material of the first part fit tightly to the thumb.

The above described orthosis presents the advantage that it can be sold in a partially molded form, be personalised later on and still show the desired properties, i.e. that its shape can be adapted to the patients' body part to be covered by it. The orthosis however remains available at reasonable cost as the part that needs no personalisation is made of a cheaper material. The personalised orthoses that are commercially available are either entirely made of thermoplastic material as a consequence of which they are expensive, or have a standard shape and are available in only one single or a few sizes which often insufficiently fit the shape and size of the body part that needs fixation, giving bad positioning of the part to be immobilised.

In the above described immobilisation device 5 and orthosis 10, the material of which the first part 1, 11 and the second part 2, 12 are made may be interchanged if it is envisaged to immobilise a different body part.

The immobilisation device 5, 10 of the present invention presents the advantage that it may be re-shaped after having been used for a period of time. The re-shaping is done by 1) re-heating the device 5, 10 to a temperature which corresponds to the melting point of the first part thermoplastic material, 2) applying the device 5, 10 to the body part to be covered by it, 0.3) shaping the device to follow the contours of the body part to be covered by it and 4) allowing the device to cool.

By combining two materials as described above, a immobilisation device can be obtained which may be personalised, which is re-sizeable and re-mouldable, and yet provides improved comfort to the patient, combined with improved fixation and larger design freedom. Also, the device is available at a reasonable price.

From the above given description it should have become clear that the hybrid immobilisation device of this invention is suitable for use in a wide variety of applications. The hybrid immobilisation device of this invention is suitable for use in radiation therapy and diagnostic imaging, where it is a prerequisite that the position of the body part to be treated is restrained within certain small limits, and that reproducible positioning with high accuracy may be ensured. The hybrid immobilisation device and the hybrid orthoses of this invention are suitable for application to the majority of the human or animal body. The hybrid immobilisation device and the hybrid orthoses of this invention may be used in the immobilisation of an entire arm or only the upper or lower part thereof, a hand, the combination of arm and hand, a leg or only the upper or lower part thereof, the foot or any other body part. The person skilled in the art will be capable of selecting from the existing second plastic materials, the material showing the strength and rigidity required for the specific application.

In a further embodiment of this invention, the immobilisation device 5, 10 may comprise means for exerting a predetermined force to the body part to be immobilised in view of pulling this part towards a surface supporting the body part or in view of pulling two or more parts of the immobilisation device towards each other and fix the body part between them. This is usually done to restrain the movement of the body part to be immobilised within the immobilisation device. It is noted that the device may further comprises means for adjusting the pulling force.

The invention claimed is:

1. A hybrid immobilisation device which is provided to cover at least a part of a patient's body that needs to be supported and/or immobilised, the immobilisation device comprising at least one first part (1, 11) and at least one second part (2, 12) which are connected to each other, the first part (1) being provided to at least partly cover the body part to be immobilised and being made of a material comprising a first thermoplastic material having a first melting temperature T1, the second part (2) being provided to at least partly cover the body part covered by the first part and being made of a second material comprising a plastic material having a second melting temperature T2, wherein T2>T1 to allow for a separate moulding of the first part (1) after the first and second part have been assembled, the first part (1) being connected to the second part (2) in such a way that the first thermoplastic material and the second plastic material at least partly overlap, wherein the first melting temperature T1 is below 100° C. such that it can be supported by the body part to be immobilized to enable direct moulding on the body part, and wherein the second part is provided to fix the position of the first part with respect to the patient's body and/or a support or diagnostic or therapeutic device.

2. The hybrid immobilisation device as claimed in claim 1, wherein the first material has a first density and the second material has a second density which is different from the first density.

3. The hybrid immobilisation device as claimed in claim 2, wherein the second material has a second density which is lower than the first density of the first material.

4. The hybrid immobilisation device as claimed in claim 1, wherein the first part (1) is made of a first thermoplastic material selected from the group of polyurethane; polyisoprene; polyester in particular polycaprolactone; a blend of one of these materials with another polymer, copolymers or blends or combinations of two or more of these materials.

5. The hybrid immobilisation device as claimed in claim 1, wherein the second part (2, 12) is made of a plastic material selected from the group of thermosetting or thermoplastic materials or a combination or mixture of two or more of such materials.

6. The hybrid immobilisation device as claimed in claim 1, wherein the second part (2, 12) is made of a plastic material selected from the group of polyolefins, in particular polyethylene, polypropylene, or ethylene-propylene copolymers; poly-ethylvinylacetate; polyvinylchloride; polystyrene; polyamide; polyacrylate or polymethacrylate, polyester in particular polyethyleneterephtalate, or polyurethane or polycaprolactone or copolymers or blends of two or more of these materials or a foam thereof, or an expanded form of these materials.

7. The hybrid immobilisation device as claimed in claim 1, wherein the first and second part (1, 2, 11, 12) are respectively made of a first and a second thermoplastic material.

8. The hybrid immobilisation device as claimed in claim 1, wherein the second part (2, 12) is made of a transparent thermoplastic material.

9. The hybrid immobilisation device as claimed in claim 1, wherein the first (1, 11) and second (2, 12) part are connected to each other by means of welding, gluing, melting together, stitching.

10. The hybrid immobilisation device as claimed in claim 1, wherein at least part of the first part (1) comprises thermoplastic material associated with at least one further material (4, 6).

11. The hybrid immobilisation device as claimed in claim 1, wherein at least part of the second part (2) comprises plastic material associated with at least one further material (4, 6).

12. The hybrid immobilisation device as claimed in claim 11, wherein the further material is selected from the group of radiation absorption material, radiation reflecting material, water absorbing material, foam material, a radiation detector or two or more of those.

13. An immobilisation mask for immobilising a patient in radiation therapy and diagnostic imaging, wherein the immobilisation mask comprises the hybrid immobilisation device as claimed in claim 1.

14. An orthosis for immobilising one or more limbs in a pre-determined position, wherein the orthosis comprises the hybrid immobilisation device as claimed in claim 1.

15. The hybrid immobilisation device as claimed in claim 1, wherein said first thermoplastic material has a melting point between 55° C.-70° C.

* * * * *